United States Patent [19]

Doria et al.

[11] 4,159,330

[45] Jun. 26, 1979

[54] 2-DISUBSTITUTED PHENYL-3,4-DIHYDRO-4-OXO-QUINAZO- LINE DERIVATIVES AND PROCESS FOR THEIR PREPARATION

[75] Inventors: Gianfederico Doria, Milan; Ciriaco Romeo, Serino; Piernicola Giraldi, Milan; Francesco Lauria, Milan; Maria L. Corno, Milan; Piero Sberze, Varese; Marcello Tibolla, Canale d'Agordo, all of Italy

[73] Assignee: Carlo Erba S.p.A., Milan, Italy

[21] Appl. No.: 857,012

[22] Filed: Dec. 2, 1977

Related U.S. Application Data

[63] Continuation-in-part of Ser. No. 738,221, Nov. 2, 1976.

[30] Foreign Application Priority Data

Apr. 19, 1977 [IT] Italy .............................. 22571 A/77
May 17, 1977 [IT] Italy .............................. 23624 A/77
Sep. 22, 1977 [IT] Italy .............................. 27834 A/77

[51] Int. Cl.$^2$ .................. A61K 31/505; C07D 239/91
[52] U.S. Cl. .............................. 424/251; 260/558 P; 260/558 R; 424/248.53; 424/248.55; 544/92; 544/94; 544/116; 544/289; 560/42; 562/451

[58] Field of Search ............... 544/289, 116; 424/251, 424/248.53, 248.55

[56] References Cited

U.S. PATENT DOCUMENTS

| 3,998,951 | 12/1976 | Harnish et al. ................. 424/251 |
| 4,071,516 | 1/1978 | Schwarz ........................... 544/116 |
| 4,099,002 | 7/1978 | Inaba et al. ..................... 544/116 |

FOREIGN PATENT DOCUMENTS

830510 12/1969 Canada ................................... 544/289

OTHER PUBLICATIONS

Yamamoto et al., Chemical Abstracts, (1975), vol. 83: 28267e, p. 516.

Primary Examiner—Donald G. Daus
Assistant Examiner—David E. Wheeler
Attorney, Agent, or Firm—Murray & Whisenhunt

[57] ABSTRACT

3,4-Dihydro-4-oxo-quinazoline derivatives substituted in the 2-position by a substituted phenyl group are disclosed. The derivatives possess anti-allergy properties and can be used for the treatment of allergic conditions.

22 Claims, No Drawings

2-DISUBSTITUTED PHENYL-3,4-DIHYDRO-4-OXO-QUINAZOLINE DERIVATIVES AND PROCESS FOR THEIR PREPARATION

This application is a continuation-in-part of copending application Ser. No. 738,221 filed on Nov. 2, 1976. The compounds which are claimed in the present application, unexpectedly exhibit greatly increased activity levels as compared to the compounds specifically disclosed in the copending application Ser. No. 738,221.

The present invention relates to 2-disubstituted phenyl-3,4-dihydro-4-oxo-quinazoline derivatives, to a process for their preparation and to pharmaceutical compositions containing them. The present invention provides compounds of the following formula (I)

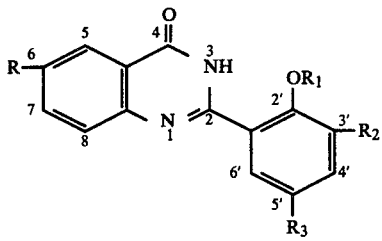

wherein
R is esterified or free carboxy;
$R_1$ is
(a) $C_1$–$C_4$ alkyl, optionally substituted by $C_1$–$C_2$ alkoxy; or
(b) $C_3$–$C_4$ alkenyl;
$R_2$ is hydrogen, methyl or $C_1$–$C_2$ alkoxy;
$R_3$ is
(a') hydrogen;
(b') $C_1$–$C_6$ alkoxy, optionally substituted by $C_1$–$C_2$ alkoxy;
(c') $C_2$–$C_4$ alkyl; or
(d') $C_3$–$C_4$ alkenyloxy,
wherein one of $R_2$ and $R_3$ is hydrogen and the other is different from hydrogen and wherein, when R is methyl and $R_2$ is hydrogen, $R_3$ is different from unsubstituted methoxy; and the pharmaceutically acceptable salts thereof.

It is to be noted that the above definition of the compounds of the invention includes all the possible isomers and stereoisomers as well as their mixtures.

The alkyl, alkenyl, alkoxy and alkenyloxy groups may be branched or straight chain.

When R is an esterified carboxy group, it is preferably a $C_2$–$C_{12}$ carbalkoxy group, in particular a $C_2$–$C_7$ carbalkoxy group, which may be unsubstituted or substituted by a

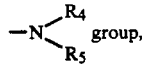

wherein each of $R_4$ and $R_5$ is independently hydrogen or $C_1$–$C_4$ alkyl, preferably $C_1$–$C_2$ alkyl, or $R_4$ and $R_5$, taken together with the nitrogen atom, form a N-pyrrolidinyl, piperidino, or morpholino radical.

When $R_3$ is $C_2$–$C_4$ alkyl, it is preferably ethyl; when $R_3$ is $C_1$–$C_6$ alkoxy, it is preferably $C_1$–$C_3$ alkoxy.

When $R_3$ is $C_3$–$C_4$ alkenyloxy, it is preferably allyloxy. R is preferably a free carboxy group or a 2-(N,N-diethylamino)-ethoxy-carbonyl group or a 2-(N,N-dimethylamino)-ethoxy-carbonyl group or a 2-(1-pyrrolidinyl)-ethoxycarbonyl group or a salified carboxy group.

Particularly preferred compounds of the invention are those of formula (I) wherein R is a free carboxy group, a 2-(N,N-diethylamino)-ethoxy-carbonyl group, a 2-(N,N-dimethylamino)-ethoxy-carbonyl group, a 2-(1-pyrrolidinyl)-ethoxycarbonyl group or a salified carboxy group, $R_1$ is $C_1$–$C_4$ alkyl, preferably $C_1$–$C_2$ alkyl, $R_2$ is $C_1$–$C_2$ alkoxy, preferably methoxy, and $R_3$ is hydrogen.

Examples of pharmaceutically acceptable salts are in particular those either with inorganic bases, such as sodium potassium, calcium and aluminium hydroxides, or with organic bases, such as, lysine, triethanolamine, triethylamine, dibezylamine, procaine, diethanolamine, N,N'-dibenzylethylenediamine, N-methyl-N-benzylamine, N,N-di-(2-ethyl-hexyl)-amine, N-ethylpiperidine, N-ethylmorpholine, piperidine, N,N-diethylaminoethylamine, β-phenethylamine, N-benzyl-β-phenethylamine, N-benzyl-N,N-dimethylamine and the other acceptable organic amines.

Also the salts with inorganic acids, e.g. hydrochloric, hydrobromic and sulphuric acids as well as those with organic acids, e.g. citric, tartaric, maleic, fumaric, malic, methanesulphonic and ethanesulphonic acids are included in the present invention. Preferred salts are the sodium and potassium salts of the compounds of formula (I) wherein R is a free carboxy group, as well as the hydrochlorides of the basic esters, e.g. the 2-(N,N-diethylamino)-ethyl and 2-(N,N-dimethylamino)-ethyl esters.

Examples of particularly preferred compounds of the invention are:
6-carboxy-2-(2',3'-dimethoxy-phenyl)-3,4-dihydro-4-oxo-quinazoline;
6-carboxy-2-(2'-ethoxy-3'-methoxy-phenyl)-3,4-dihydro-4-oxo-quinazoline;
6-carboxy-2-(2'-isopropoxy-3'-methoxy-phenyl)-3,4-dihydro-4-oxo-quinazoline;
6-carboxy-2-(2'-butoxy-3'-methoxy-phenyl)-3,4-dihydro-4-oxo-quinazoline;
6-carboxy-2-(2',3'-diethoxy-phenyl)-3,4-dihydro-4-oxo-quinazoline;
6-carboxy-2-(2'-ethoxy-3'-methyl-phenyl)-3,4-dihydro-4-oxo-quinazoline;
6-carboxy-2-(2'-ethoxy-5'-methoxy-phenyl)-3,4-dihydro-4-oxo-quinazoline;
6-carboxy-2-(2'-ethoxy-5'-propoxy-phenyl)-3,4-dihydro-4-oxo-quinazoline;
6-carboxy-2-(2'-methoxy-5'-ethoxy-phenyl)-3,4-dihydro-4-oxo-quinazoline;
6-carboxy-2-(2'-methoxy-5'-allyloxy-phenyl)-3,4-dihydro-4-oxo-quinazoline;
6-carboxy-2-(2'-ethoxy-5'-isopropoxy-phenyl)-3,4-dihydro-4-oxo-quinazoline;
6-carboxy-2-(2'-ethoxy-5'-ethyl-phenyl)-3,4-dihydro-4-oxo-quinazoline;
6-[2-(N,N-diethylamino)-ethoxy-carbonyl]-2-(2'-ethoxy-3'-methoxy-phenyl)-3,4-dihydro-4-oxo-quinazoline;
6-[2-(N,N-dimethylamino)-ethoxy-carbonyl]-2-(2'-ethoxy-3'-methoxy-phenyl)-3,4-dihydro-4-oxo-quinazoline;
6-[2-(1-pyrrolidinyl)-ethoxy-carbonyl]-2-(2'-ethoxy-3'-methoxy-phenyl)-3,4-dihydro-4-oxo-quinazoline, as well as the pharmaceutically acceptable salts thereof, in particular the sodium salts and the hydrochlorides of the basic esters (in particular of those with 2-(N,N-diethylamino)-ethanol, 2-(N,N-dimethylamino)-ethanol, 2-(1-pyrrolidinyl)-ethanol and the esters, in particular the ethyl, isopropyl, t-butyl, hexyl esters.

The compounds of the invention are prepared by a process comprising:

(a) cyclizing a compound of formula (II)

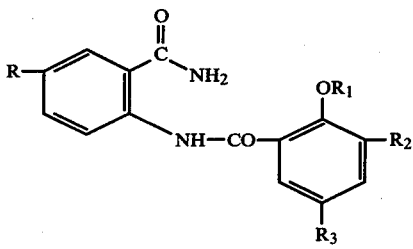

wherein R, $R_1$, $R_2$, $R_3$ are as defined above, or a salt thereof; or (b) oxidizing a compound of formula (III)

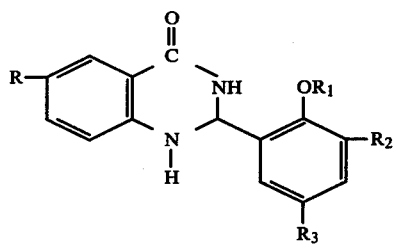

wherein R, $R_1$, $R_2$, $R_3$ are as defined above, or a salt thereof; and, if desired, converting a compound of formula (I) into another compound of formula (I) by known methods and/or, if desired, converting a compound of formula (I) into a pharmaceutically acceptable salt and/or, if desired, converting a salt into a free compound and/or, if desired, resolving a mixture of isomers into the single isomers. The cyclization of the compounds of formula (II) may be carried out, e.g., at a temperature ranging from room temperature to about 200° C., by treatment with a basis such as, for example, ammonium, sodium or potassium hydroxide, either in the absence of solvents or in the presence of a solvent such as, for example, tetrahydrofuran, dioxane, dimethylformamide and their mixtures.

Alternatively, the cyclization of the compounds of formula (II) may be carried out by treatment with a dehydrating agent such as, for example, acetic anhydride, $PCl_3$, $POCl_3$, polyphosphoric acid, dicyclohexylcarbodiimide, either in the absence of solvents or in the presence of a solvent, such as, for example, benzene, toluene, xylene, pyridine, tetrahydrofuran, dioxane, acetic acid, dimethylformamide, at a temperature ranging from about 0° C. to about 200° C. The oxidation of the compounds of formula (III) may be carried out, for example, with potassium permanganate in acetone or with chromium trioxide in acetic acid at a temperature ranging from about 0° C. to about 30° C.

As stated above, a compound of formula (I) may be converted into another compound of formula (I) by known methods. For example, a compound of formula (I), wherein R is an esterified carboxy group, may be converted into a compound of formula (I), wherein R is carboxy, by basic hydrolysis, using, e.g., sodium or potassium hydroxide, in a solvent such as water or a lower aliphatic alcohol, and operating at a temperature ranging from the room temperature to about 150° C.; the same reaction may be carried out by treatment with lithium bromide in dimethylformamide at a temperature higher than 50° C.

A compound of formula (I) wherein R is carboxy, may be converted into a compound of formula (I) wherein R is an esterified carboxy group, e.g., a carbalkoxy group, by esterification, for example, by reaction of the alkaline salt of the acid with the suitable alkyl halide, in an inert solvent such as acetone, dioxane, dimethylformamide, hexamethylphosphorotriamide at a temperature ranging from about 0° C. to about 100° C.

Also the optional salification of a compound of formula (I) as well as the conversion of a salt into the free compound and the resolution of a mixture of isomers into the single isomers may be effected by conventional methods.

The compounds of formula (II) may be prepared, for example:

(a') by reaction of a compound of formula (IV)

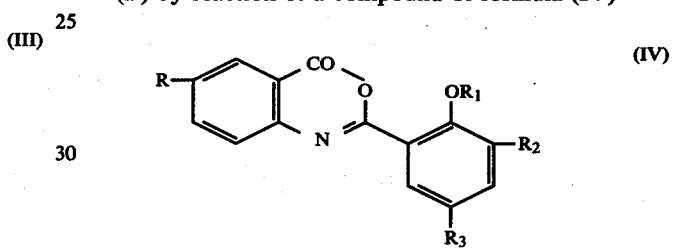

wherein R, $R_1$, $R_2$ and $R_3$ are as defined above, with ammonium hydroxide; this reaction is preferably performed at a temperature ranging from the room temperature to 200° C., either in the absence of solvents or in an inert organic solvent such as lower aliphatic alcohols, dioxane and dimethylformamide;

(b') by reaction of a compound of formula (V)

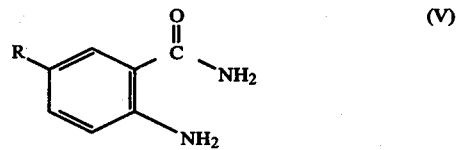

wherein R is as defined above, with a compound of formula (VI)

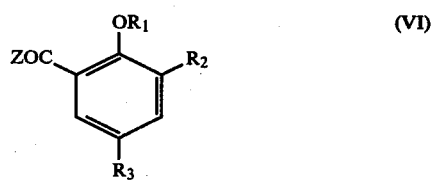

wherein $R_1$, $R_2$ and $R_3$ are as defined above and Z is chlorine or bromine; this reaction is preferably performed at a temperature ranging from the room temperature to 150° C., using a basis such as, for example, sodium bicarbonate, sodium carbonate, pyridine, triethylamine as acid acceptor, operating either in the presence of a solvent such as, e.g., benzene, toluene, xylene, pyridine, dioxane, dimethylformamide or in the absence of solvents.

The compounds of formula (III) may be prepared, for example, by reaction of the compounds of formula (V) with an aldehyde of formula (VII)

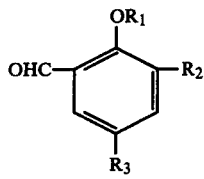

wherein $R_1$, $R_2$ and $R_3$ are as defined above, in an inert solvent such as, for example, benzene, toluene, xylene, dioxane, ethanol, dimethoxyethane, bis-(2-methoxyethyl)ether, dimethylformamide and in the presence of a basic or acid catalyst such as piperidine, hydrochloric acid, sulphuric acid, p-toluensulphonic acid, at a temperature ranging from the room temperature to about 150° C.

The compounds of formula (IV) may be in turn prepared, for example, by heating a compound of formula (VIII)

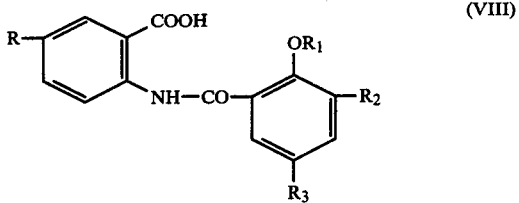

wherein R, $R_1$, $R_2$ and $R_3$ are as defined above, in acetic anhydride at a temperature varying between the room temperature and the reflux temperature.

The compounds of formula (VIII) may be prepared for example by reaction of a compound of formula (IX)

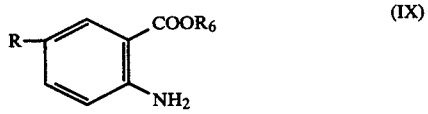

wherein R is as defined above and $R_6$ is hydrogen or alkyl, in particular $C_1$-$C_4$ alkyl, with a compound of formula (VI), at a temperature varying between room temperature and 150° C., either in the presence of a solvent such as benzene, toluene, dioxane, pyridine or in the absence of solvents, using a basis such as sodium bicarbonate, sodium carbonate, pyridine, triethylamine, as acid acceptor, and by subsequent basic hydrolysis of the ester group, i.e., when $R_6$ is alkyl, with sodium or potassium hydroxide in a solvent such as water, lower aliphatic alcohols, in particular ethanol, dioxane and their mixtures at a temperature ranging from 10° C. to 100° C. The compounds of formula (V) may be prepared by known methods, for example, by reduction of the corresponding nitro-derivatives or by reaction of a compound of formula (X)

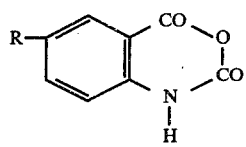

wherein R is as defined above, with ammonium hydroxide, either in the absence of solvents or in the presence of organic solvents such as methanol, ethanol, dioxane, dimethylformamide, tetrahydrofuran, at a temperature ranging from −30° C. to 200° C. The compounds of formula (VI) are known compounds and they may be prepared by conventional methods.

The compounds of formula (X) may be in turn prepared from a compound of formula (IX), wherein $R_6$ is hydrogen, by one of the following methods:

(a″) by reaction with phosgene at room temperature in an acidic aqueous medium;

(b″) by reaction with ethyl chloroformate, at a temperature ranging from 50° C. to 120° C., either in the absence or in the presence of solvents such as, dioxane, benzene, toluene, xylene, to obtain the corresponding N-carbethoxy derivative, and by subsequent cyclization, which may be carried out by using an excess of ethyl chloroformate or with acetyl chloride or with PBr₃, at a temperature ranging from 50° C. to 150° C.

The compounds of formula (IX) are known compounds and may be prepared by known methods, for example, by reduction, in a conventional manner, of the corresponding nitro-derivatives. Also the compounds of formula (VII) are known compounds.

The compounds of the invention possess anti-allergic activity, as is shown by the fact that they are active in the passive cutaneous anaphylaxis (PCA) test in rats, according to Goose Y. and Blair A.M.Y.N. (Immunology, 1969, 16:749).

They can be therefore used in prevention and treatment of bronchial asthma, allergic rhinitis, hay fever, urticaria and dermatosis.

An important peculiarity of the compounds of the invention is that they exhibit high levels of antiallergic activity also when orally administered, as is shown in the following Table, where the potency ratio of a number of compounds of the invention, reported with respect to the compounds 6-carboxy-2-(2'-methoxyphenyl)-3,4-dihydro-4-oxo-quinazoline (K 11695) and 6-carboxy-2-(2'-methoxy-5'-methyl-phenyl)-3,4-dihydro-4-oxo-quinazoline (K 11963), which compounds are two active quinazoline derivatives among those described in German Offenlegungsschrift No. P26 54 215.4, corresponding to U.S. patent application Ser. No. 738,221 of Nov. 2, 1976. To the antiallergic activity of the compound K 11695 the conventional value 1 was given.

In the following Table the compounds of the invention are identified by the codes:

K 13261: 6-carboxy-2-(2'-ethoxy-3'-methoxy-phenyl)-3,4-dihydro-4-oxo-quinazoline;

K 13323: 6-carboxy-2-(2'-methoxy-5'-allyloxy-phenyl)-3,4-dihydro-4-oxo-quinazoline;

K 11944: 6-carboxy-2-(2'-ethoxy-5'-methoxy-phenyl)-3,4-dihydro-4-oxo-quinazoline;

K 13300: 6-carboxy-2-(2',3'-dimethoxy-phenyl)-3,4-dihydro-4-oxo-quinazoline;

K 13251: 6-carboxy-2-(2'-ethoxy-5'-isopropoxy-phenyl)-3,4-dihydro-4-oxo-quinazoline;

K 13330: 6-carboxy-2-(2'-methoxy-5'-ethoxy-phenyl)-3,4-dihydro-4-oxo-quinazoline;

K 13336: 6-carboxy-2-(2',3'-diethoxy-phenyl)-3,4-dihydro-4-oxo-quinazoline;

K 11966: 6-carboxy-2-(2'-ethoxy-3'-methyl-phenyl)-3,4-dihydro-4-oxo-quinazoline;

K 13349: 6-[2-(N,N-diethylaminoethoxy)carbonyl]-2-(2'-ethoxy-3'-methoxy-phenyl)-3,4-dihydro-4-oxo-quinazoline.

TABLE

| Compound | Potency ratio | Fiducial limits for P = 0.95 |
|---|---|---|
| K 11695 | 1 | — |
| K 11963 | 1.91 | 1.10–3.37 |
| K 13261 | 38.90 | 26.44–58.20 |
| K 13323 | 10.16 | 6.90–15.06 |
| K 11944 | 13.54 | 9.25–20.51 |
| K 13300 | 5.70 | 3.58–9.23 |
| K 13251 | 5.28 | 3.36–8.42 |
| K 13330 | 8.04 | 4.30–15.72 |
| K 13336 | 6.66 | 3.57–12.89 |
| K 11966 | 4.25 | 2.75–6.73 |
| K 13349 | 51.76 | 33.48–82.32 |

The antiallergic activity was determined by the inhibition of the IgE-mediated PCA according to Goose J. and Blair A.M.J.N. (loc. cit.) using homocytotropic antibodies raised in rats following the method of Mota I., Immunology, 7, 681, (1964).

The tested compounds were administered per os 15 minutes before the administration of the antigen: at least 6 rats were used for each dose.

The potency ratios were calculated according to the method of Finney, D. J. (1952), Statistical Method in Biological Assay, C. Griffin, London, page 118.

Seven days indicative acute toxicity after oral administration was assessed for the compounds of the invention. For Example, the following $LD_{50}$ values were obtained:

K 13261: $LD_{50}$>400 mg/kg in rats;
K 11944: $LD_{50}$>800 mg/kg in rats;
K 13300: $LD_{50}$>800 mg/kg in mice;
K 11966: $LD_{50}$>800 mg/kg in mice.

The codes K 13261, K 11944, K 13300 and K 11966 were used to identify the compounds of the invention as specified above.

The compounds of the invention may be administered in conventional manner, for instance, orally and parenterally at a daily dosage preferably of 0.5 to 15 mg/kg, or by inhalation, preferably at a daily dosage of 0.5 to 100 mg, preferably 0.5 to 25 mg, or by topical application.

The nature of the pharmaceutical compositions containing the compounds of this invention in association with pharmaceutically acceptable carriers or diluents will, of course, depend upon the desired mode of administration.

The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, or creams, or lotions for topical use.

Thus, for oral administration, the pharmaceutical compositions containing the compounds of this invention, are preferably tablets, pills or gelatine capsules which contain the active substance together with diluents, such as, for example, lactose, dextrose, sucrose, mannitol, sorbitol, cellulose; lubricants, for instance, silica, talc, stearic acid, magnesium or calcium stearate, and/or polyethylene glycols; or they may also contain binders, such as, for example, starches, gelatine, methylcellulose, carboxymethylcellulose, gum-arabic, tragacanth, polyvinylpyrrolidone, disintegrating agents, such as, for instance, starches, alginic acid, alginates, sodium starch glycolate; effervescing mixtures; dye-stuffs; sweeteners; wetting agents, such as, for instance, lecithin, polisorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

For the treatment of allergic asthma, the compounds of the invention are also administered by inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquified propellant, such as, dichlorodifluoromethane or dichlorotetrafluoroethane to be administered from a pressurized container, i.e., an aerosol dispenser. When the medicament is not soluble in the propellant, it may be necessary to add a co-solvent, such as, ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g., lecithin.

The compounds of the invention may also be administered in the form of powders by means of a suitable insufflator device and in this case the fine particle sized powders of the active ingredient may be mixed with a diluent material such as lactose.

Furthermore, the compounds of this invention may also be administered by intradermal or intravenous injection in the conventional manner or by suppositories.

In addition to the internal administration, the compounds of this invention may find use in compositions for topical application, e.g. as creams, lotions or pastes for use in dermatological treatments. For these compositions the active ingredient may be mixed with conventional oleaginous or emulsifying excipients.

The following examples illustrate but do not limit the present invention.

EXAMPLE 1

Dimethyl-4-amino-isophthalate (5 g) in 50 ml of dioxane and 10 ml of anhydrous pyridine is treated with 7.5 g of 2-ethoxy-3-methoxybenzoyl chloride at room temperature, overnight. After dilution with water, the precipitate is collected, dissolved in ethyl acetate, and washed with 5% NaHCO₃ and then with water. After evaporation to dryness under vacuum, the material is crystallized from isopropyl ether, yielding dimethyl-4-(2'-ethoxy-3'-methoxy-benzoylamino)-isophthalate (9 g; m.p. 113°–115° C.), which is dissolved in 80 ml of dioxane and treated with 70 ml of 1N NaOH at room temperature for 4 hours. After acidification with diluted HCl, the precipitate is collected under vacuum and washed with water until neutral. The yield is 7.4 g of 4-(2'-ethoxy-3'-methoxy-benzoylamino)-isophthalic acid (m.p.=244°–246° C.), which are treated with 10 ml of acetic anhydride at the reflux temperature for 10'.

After cooling, dilute with 60 ml of isopropyl ether and filter.

The yield is 5 g of 6-carboxy-2-(2'-ethoxy-3'-methoxy-phenyl)-4H-3,1-benzoxazin-4-one (m.p.=175°–177° C.), which are reacted at room temperature first with 70 ml of 32% ammonium hydroxide for 4 hours and then with 20 ml of 2N NaOH overnight. After acidification with 4N HCl, the precipitate is filtered off and crystallized from ethanol to give 6-carboxy-2-(2'-ethoxy-3'-methoxy-phenyl)-3,4-dihydro-4-oxo-quinazoline (3 g; m.p. 228°–229° C.).

Analogously, the following compounds were obtained:
6-carboxy-2-(2',3'-dimethoxy-phenyl)-3,4-dihydro-4-oxo-quinazoline, m.p. 269°–271° C.;
6-carboxy-2-(2'-isopropoxy-3'-methoxy-phenyl)-3,4-dihydro-4-oxo-quinazoline, m.p. 278°–280° C.;
6-carboxy-2-(2'-butoxy-3'-methoxy-phenyl)-3,4-dihydro-4-oxo-quinazoline, m.p. 211°–212° C.;
6-carboxy-2-[2'-(2-ethoxyethoxy)-3'-methoxy-phenyl]-3,4-dihydro-4-oxo-quinazoline, m.p. 206°–207° C.

EXAMPLE 2

Proceeding as described in Example 1, starting from the suitable 2-alkoxy-3-ethoxy-benzoyl-chlorides, the following compounds were prepared:
6-carboxy-2-(2'-methoxy-3'-ethoxy-phenyl)-3,4-dihydro-4-oxo-quinazoline, m.p. 272°–273° C.;
6-carboxy-2-(2',3'-diethoxy-phenyl)-3,4-dihydro-4-oxo-quinazoline, m.p. 233°–234° C.

EXAMPLE 3

Proceeding as described in Example 1, starting from the suitable 2-alkoxy-5-methoxy-benzoyl-chlorides, the following compounds were prepared:
6-carboxy-2-(2'-ethoxy-5'-methoxy-phenyl)-3,4-dihydro-4-oxo-quinazoline, m.p. 269°–271° C.;
6-carboxy-2-(2'-isopropoxy-5'-methoxy-phenyl)-3,4-dihydro-4-oxo-quinazoline, m.p. 280°–282° C.;
6-carboxy-2-(2'-butoxy-5'-methoxy-phenyl)-3,4-dihydro-4-oxo-quinazoline, m.p. 244°–245° C.

EXAMPLE 4

4-amino-isophthalic acid (17 g) is refluxed in 800 ml of methanol and 39 ml of $BF_3$ etherate for 18 hours. After concentration under vacuum, dilute with water and filter. The precipitate is partitioned between 250 ml of ethyl acetate and 250 ml of 5% $NaHCO_3$. The aqueous phase is separated off and acidified and the precipitate filtered out and washed with water until neutral. This yields 12 g of 2-amino-5-carbomethoxybenzoic acid, which are then reacted with 60 ml of ethyl chlorocarbonate in 80 ml of dioxane under reflux for 20 hours. Add 48 ml of acetyl chloride and reflux for 72 hours. Concentrate the suspension obtained under vacuum, dilute with ethyl ether and filter. This gives 10 g of 5-carbomethoxy-isatoic anhydride (m.p. 275°–278° C.) which are treated with 25 ml of 32% ammonium hydroxide in 25 ml of dimethylformamide at room temperature for 30'. After dilution with water, the precipitate is filtered off and washed until neutral. 2-amino-5-carbomethoxybenzamide (8.1 g) is obtained, which is dissolved in 80 ml of dioxane and 10 ml of pyridine and reacted with 14 g of 2-ethoxy-3-methyl-benzoyl-chloride at room temperature for 16 hours. After dilution with water, filter the precipitate and wash it until neutral. Crystallize from ethanol, yielding 9.4 g of 2-(2'-ethoxy-3'-methyl-benzoylamino)-5-carbomethoxybenzamide, which are treated with 45 ml of 2N sodium hydroxide in 45 ml of dioxane at room temperature for 8 hours.

After dilution with water and acidification, the precipitate is filtered and washed with hot ethanol to yield 7.4 g of 6-carboxy-2-(2'-ethoxy-3'-methyl-phenyl)-3,4-dihydro-4-oxo-quinazoline, m.p. 240°–241° C.

Analogously the following compound was obtained:
6-carboxy-2-(2'-methoxy-3'-methyl-phenyl)-3,4-dihydro-4-oxo-quinazoline, m.p. 252°–253° C.

EXAMPLE 5

Proceeding as described in Example 1, starting from the suitable 2,5-dialkoxy-benzoyl-chlorides, the following compounds were prepared:
6-carboxy-2-(2',5'-diethoxy-phenyl)-3,4-dihydroy-4-oxo-quinazoline, m.p. 291°–292° C.;
6-carboxy-2-(2'-methoxy-5'-ethoxy-phenyl)-3,4-dihydro-4-oxo-quinazoline, m.p. 27°–5° C.;
6-carboxy-2-(2'-methoxy-5'-isopropoxy-phenyl)-3,4-dihydro-4-oxo-quinazoline, m.p. 279°–280° C.;
6-carboxy-2-(2'-ethoxy-5'-isopropoxy-phenyl)-3,4-dihydro-4-oxo-quinazoline, m.p. 225°–227° C.;
6-carboxy-2-(2',5'-diisopropoxy-phenyl)-3,4-dihydro-4-oxo-quinazoline, m.p. 216–217° C.;
6-carboxy-2-(2'-methoxy-5'-propoxy-phenyl)-3,4-dihydro-4-oxo-quinazoline, m.p. 275°–277° C.;
6-carboxy-2-(2'-ethoxy-5'-propoxy-phenyl)-3,4-dihydro-4-oxoquinazoline, m.p. 258°–260° C.;
6-carboxy-2-(2'-methoxy-5'-allyloxy-phenyl)-3,4-dihydro-4-oxo-quinazoline, m.p. 251°–253° C.;
6-carboxy-2-(2'-ethoxy-5'-allyloxy-phenyl)-3,4-dihydro-4-oxo-quinazoline, m.p. 244°–245° C.;
6-carboxy-2-[2'-methoxy-5'-(2-ethoxyethoxy)-phenyl]-3,4-dihydro-4-oxo-quinazoline, m.p. 239°–240° C.

EXAMPLE 6

Proceeding as described in Example 1, starting from the suitable 2-ethoxy-5-alkyl-benzoyl-chlorides, the following compounds were prepared:
6-carboxy-2-(2'-ethoxy-5'-ethyl-phenyl)-3,4-dihydro-4-oxo-quinazoline, m.p. 272°–274° C.;
6-carboxy-2-(2'-ethoxy-5'-propyl-phenyl)-3,4-dihydro-4-oxo-quinazoline, m.p. 280°–282° C.;
6-carboxy-2-(2'-ethoxy-5'-butyl-phenyl)-3,4-dihydro-4-oxo-quinazoline, m.p. 249°–251° C.

EXAMPLE 7

2-amino-5-carbomethoxy-benzamide (4 g), obtained as described in Example 4, is reacted with 4.5 g of 2-ethoxy-3-methoxy-benzaldehyde in the presence of 0.2 ml of piperidine in 150 ml of xylene and refluxed for 4 hours. After cooling, the precipitate is filtered out and washed with benzene. The yield is 3.9 g of 6-carboxmethoxy-2-(2'-ethoxy-3'-methoxyphenyl)-1,2,3,4-tetrahydro-4-oxo-quinazoline, which are dissolved in 250 ml of acetone and oxidized at 0°–5° C. for 3 hours by a gradual addition of 2.3 g of finely powdered potassium permanganate. An excess of sodium bisulfite is added and after one hour the inorganic precipitate is filtered out and the acetone solution evaporated to dryness to give a residue which is crystallized from ethanol. The yield is 2.6 g of 6-carbomethoxy-2-(2'-ethoxy-3'-methoxyphenyl)-3,4-dihydro-4-oxo-quinazoline, m.p. 165°–167° C., which are treated with 12 ml of 1N NaOH in 25 ml of dioxane at room temperature for 16 hours.

After dilution with water and acidification, 6-carboxy-2-(2'-ethoxy-3'-methoxyphenyl)-3,4-dihydro-4-oxo-quinazoline (2.1 g; m.p. 228°–229° C.), is obtained.

Analogously, the following compounds were obtained:
6-carboxy-2-(2',3'-dimethoxy-phenyl)-3,4-dihydro-4-oxo-quinazoline, m.p. 269°–271° C.;
6-carboxy-2-(2',3'-diethoxy-phenyl)-3,4-dihydro-4-oxo-quinazoline, m.p. 233°–234° C.;
6-carboxy-2-(2'-ethoxy-3'-methyl-phenyl)-3,4-dihydro-4-oxo-quinazoline, m.p. 240°–241° C.;
6-carboxy-2-(2'-ethoxy-5'-methoxy-phenyl)-3,4-dihydro-4-oxo-quinazoline, m.p. 269°–271° C.;
6-carboxy-2-(2'-ethoxy-5'-ethyl-phenyl)-3,4-dihydro-4-oxo-quinazoline, m.p. 272°–274° C.

EXAMPLE 8

6-carboxy-2-(2'-ethoxy-3'-methoxy-phenyl)-3,4-dihydro-4-oxo-quinazoline (5.8 g.), obtained as described in Example 1, is treated with an excess (2 moles/mole) of thionyl chloride in dioxane at reflux temperature for 4 hours. After cooling and concentrating to dryness under vacuum, the residue is reacted with an excess of absolute ethanol at 50° C. for 2 hours. After cooling, the precipitate is filtered and washed with ethanol and water. The yield is 5.1 g of 6-carbethoxy-2-(2'-ethoxy-3'-methoxy-phenyl)-3,4-dihydro-4-oxo-quinazoline, m.p. 168°–169° C.

Analogously, the following compounds were obtained:
6-carbethoxy-2-(2'-ethoxy-5'-methoxy-phenyl)-3,4-dihydro-4-oxo-quinazoline;
6-carbethoxy-2-(2'-methoxy-5'-allyloxy-phenyl)-3,4-dihydro-4-oxo-quinazoline.

EXAMPLE 9

6-carboxy-2-(2'-ethoxy-3'-methoxy-phenyl)-3,4-dihydro-4-oxo-quinazoline (3.6 g) is treated with hot aqueous solution of 800 mg of sodium bicarbonate. After cooling and clearing the solution by filtration, it is concentrated to a small volume and diluted with 4 volumes of acetone. Filter the precipitate and wash it with acetone. The yield is 3.4 g of the sodium salt of 6-carboxy-2-(2'-ethoxy-3'-methoxy-phenyl)-3,4-dihydro-4-oxo-quinazoline, m.p. >320° C.

Analogously, the sodium salts of the following compounds were obtained:
6-carboxy-2-(2',3'-dimethoxy-phenyl)-3,4-dihydro-4-oxo-quinazoline;
6-carboxy-2-(2',3'-diethoxy-phenyl)-3,4-dihydro-4-oxo-quinazoline;
6-carboxy-2-(2'-ethoxy-5'-methoxy-phenyl)-3,4-dihydro-4-oxo-quinazoline, m.p. >320° C.;
6-carboxy-2-(2'-ethoxy-5'-ethyl-phenyl)-3,4-dihydro-4-oxo-quinazoline;
6-carboxy-2-(2'-methoxy-5'-allyloxy-phenyl)-3,4-dihydro-4-oxo-quinazoline, m.p. >310° C.;
6-carboxy-2-(2'-ethoxy-3'-methyl-phenyl)-3,4-dihydro-4-oxo-quinazoline.

EXAMPLE 10

Proceeding as described in Example 8 and using the suitable aliphatic alcohols, the isopropyl-, tert-butyl, octyl-, hexyl-, undecyl-esters of the following compounds were obtained:
6-carboxy-2-(2',3'-dimethoxy-phenyl)-3,4-dihydro-4-oxo-quinazoline;
6-carboxy-2-(2-ethoxy-3'-methoxy-phenyl)-3,4-dihydro-4-oxo-quinazoline;
6-carboxy-2-(2'-isopropoxy-3'-methoxy-phenyl)-3,4-dihydro-4-oxo-quinazoline;
6-carboxy-2-(2'-methoxy-5'-allyloxy-phenyl)-3,4-dihydro-4-oxo-quinazoline;
6-carboxy-2-(2'-methoxy-3'-ethoxy-phenyl)-3,4-dihydro-4-oxo-quinazoline;
6-carboxy-2-(2'-methoxy-3'-methyl-phenyl)-3,4-dihydro-4-oxo-quinazoline;
6-carboxy-2-(2'-ethoxy-5'-ethyl-phenyl)-3,4-dihydro-4-oxo-quinazoline;
6-carboxy-2-(2'-ethoxy-5'-methoxy-phenyl)-3,4-dihydro-4-oxo-quinazoline.

EXAMPLE 11

6-chlorocarbonyl-2-(2'-ethoxy-3'-methoxy-phenyl)-3,4-dihydro-4-oxo-quinazoline (6.1 g) obtained as described in Example 8, is suspended in 60 ml of dioxane and treated with 4.2 ml of 2-(N,N-diethylamino)-ethanol and 1 ml of triethylamine at room temperature for 18 hours. After dilution with water and alkalinization with $K_2CO_3$, the precipitate is filtered and washed until neutral, then crystallized from ethanol. The yield is 5.5 g of the 2-(N,N-diethylamino)-ethyl ester of 6-carboxy-2-(2'-ethoxy-3'-methoxy-phenyl)-3,4-dihydro-4-oxo-quinazoline, m.p. 93°–94° C.

Analogously, the 2-(N,N-diethylamino)-ethyl esters of the following compounds were obtained:
6-carboxy-2-(2',3'-dimethoxy-phenyl)-3,4-dihydro-4-oxo-quinazoline;
6-carboxy-2-(2'-methoxy-3'-ethoxy-phenyl)-3,4-dihydro-4-oxo-quinazoline;
6-carboxy-2-(2'-isopropoxy-3'-methoxy-phenyl)-3,4-dihydro-4-oxo-quinazoline;
6-carboxy-2-[2'-(2-ethoxyethoxy)-3'-methoxy-phenyl]-3,4-dihydro-4-oxo-quinazoline;
6-carboxy-2-(2'-methoxy-5'-allyloxy-phenyl)-3,4-dihydro-4-oxo-quinazoline;
6-carboxy-2-(2'-methoxy-3'-methyl-phenyl)-3,4-dihydro-4-oxo-quinazoline;
6-carboxy-2-(2'-ethoxy-5'-methoxy-phenyl)-3,4-dihydro-4-oxo-quinazoline;
6-carboxy-2-(2'-ethoxy-5'-ethyl-phenyl)-3,4-dihydro-4-oxo-quinazoline.

EXAMPLE 12

Proceeding as described in Example 11, and using as reagents either 2-(N,N-dimethylamino)-ethanol or 2-(1-pyrrolidinyl)-ethanol, the following esters were obtained:
6-[2-(N,N-dimethylamino)-ethoxy-carbonyl]-2-(2'-ethoxy-3'-methoxy-phenyl)-3,4-dihydro-4-oxo-quinazoline, m.p. 137°–138° C.;
6-[2-(N,N-dimethylamino)-ethoxy-carbonyl]-2-(2'-ethoxy-5'-methoxy-phenyl)-3,4-dihydro-4-oxo-quinazoline;
6-[2-(N,N-dimethylamine)-ethoxy-carbonyl]-2-(2'-methoxy-5'-allyloxy-phenyl)-3,4-dihydro-4-oxo-quinazoline;
6-[2-(1-pyrrolidinyl)-ethoxy-carboyl]-2-2'-ethoxy-3'-methoxy-phenyl)-3,4-dihydro-4-oxo-quinazoline, m.p. 144°–146° C.;
6-[2-(1-pyrrolidinyl)-ethoxy-carbonyl]-2-(2'-ethoxy-5'-methoxy-phenyl)-3,4-dihydro-4-oxo-quinazoline;
6-[2-(1-pyrrolidinyl)-ethoxy-carbonyl]-2-(2'-methoxy-5'-allyloxy-phenyl)-3,4-dihydro-4-oxo-quinazoline.

EXAMPLE 13

Tablets, each weighing 150 mg and containing 50 mg of the active substance are manufactured as follows:

| Composition (for 10,000 tablets) | |
|---|---|
| 6-carboxy-2-(2'-ethoxy-3'-methoxy-phenyl)-3,4-dihydro-4-oxo-quinazoline | 500 g |
| lactose | 710 g |
| corn starch | 237.5 g |
| talc powder | 37.5 g |
| magnesium stearate | 15 g |

6-carboxy-2-(2'-ethoxy-3'-methoxy-phenyl)-3,4-dihydro-4-oxo-quinazoline, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed, and processed into tablets using punches of 8 mm diameter.

EXAMPLE 14

| Aerosol formulation: | |
|---|---|
| 6-carboxy-2-(2'-ethoxy-3'-methoxy-phenyl)-3,4-dihydro-4-oxo-quinazoline | 2 % |
| ethanol | 10 % |
| lecithin | 0.2 % |
| mixture of dichlorodifluoromethane and dichlorotetrafluoroethane (70:30 mixture) | ad 100 %. |

We claim:
1. A compound of the formula (I)

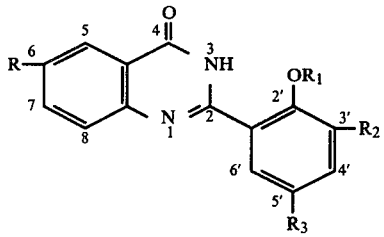

(I)

wherein
R is carboxy or COOR$_7$, wherein R$_7$ is C$_2$-C$_{12}$ alkyl unsubstituted or monosubstituted by

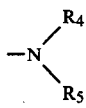

wherein each of R$_4$ and R$_5$ is independently hydrogen or C$_1$-C$_4$ alkyl, or R$_4$ and R$_5$, taken together with the nitrogen atom, form a N-pyrrolidinyl, piperidino or morpholino group;
R$_1$ is
  (a) C$_1$-C$_4$ alkyl, unsubstituted or monosubstituted by C$_1$-C$_2$ alkoxy; or
  (b) C$_3$-C$_4$ alkenyl;
R$_2$ is a hydrogen, methyl or C$_1$-C$_2$ alkoxy;
R$_3$ is
  (a') hydrogen;
  (b') C$_1$-C$_6$ alkoxy, unsubstituted or monosubstituted by C$_1$-C$_2$ alkoxy;
  (c') C$_2$-C$_4$ alkyl; or
  (d') C$_3$-C$_4$ alkenyloxy,
wherein one of R$_2$ and R$_3$ is hydrogen and the other is different from hydrogen and wherein, when R$_1$ is methyl and R$_2$ is hydrogen, R$_3$ is different from unsubstituted methoxy; and the pharmaceutically acceptable salts thereof.

2. A compound of the formula (I) wherein R is a free carboxy group, a 2-(N,N-diethylamino)-ethoxy-carbonyl group, a 2-(N,N-dimethylamino)-ethoxy-carbonyl group, a 2-(1-pyrrolidinyl)-ethoxy-carbonyl group or a salified carboxy group, R$_1$ is C$_1$-C$_4$ alkyl, R$_2$ is C$_1$-C$_2$ alkoxy and R$_3$ is hydrogen.

3. A compound of the formula (I) according to claim 2 wherein R$_1$ is C$_1$-C$_2$ alkyl.

4. A compound of the formula (I) according to claim 2 wherein R$_2$ is methoxy.

5. 6-carboxy-2-(2',3'-dimethoxy-phenyl)-3,4-dihydro-4-oxo-quinazoline and the pharmaceutically acceptable esters and salts thereof.

6. 6-carboxy-2-(2'-ethoxy-3'-methoxy-phenyl)-3,4-dihydro-4-oxo-quinazoline and the pharmaceutically acceptable esters and salts thereof.

7. 6-carboxy-2-(2'-isopropoxy-3'-methoxy-phenyl)-3,4-dihydro-4-oxo-quinazoline and the pharmaceutically acceptable esters and salts thereof.

8. 6-carboxy-2-(2'-butoxy-3'-methoxy-phenyl)-3,4-dihydro-4-oxo-quinazoline and the pharmaceutically acceptable esters and salts thereof.

9. 6-carboxy-2-(2',3'-diethoxy-phenyl)-3,4-dihydro-4-oxo-quinazoline and the pharmaceutically acceptable esters and salts thereof.

10. 6-carboxy-2-(2'-ethoxy-3'-methyl-phenyl)-3,4-dihydro-4-oxo-quinazoline and the pharmaceutically acceptable esters and salts thereof.

11. 6-carboxy-2-(2'-ethoxy-5'-methoxy-phenyl)-3,4-dihydro-4-oxo-quinazoline and the pharmaceutically acceptable esters and salts thereof.

12. 6-carboxy-2-(2'-ethoxy-5'-propoxy-phenyl)-3,4-dihydro-4-oxo-quinazoline and the pharmaceutically acceptable esters and salts thereof.

13. 6-carboxy-2-(2'-methoxy-5'-ethoxy-phenyl)-3,4-dihydro-4-oxo-quinazoline and the pharmaceutically acceptable esters and salts thereof.

14. 6-carboxy-2-(2'-methoxy-5'-allyloxy-phenyl)-3,4-dihydro-4-oxo-quinazoline and the pharmaceutically acceptable esters and salts thereof.

15. 6-carboxy-2-(2'-ethoxy-5'-isopropoxy-phenyl)-3,4-dihydro-4-oxo-quinazoline and the pharmaceutically acceptable esters and salts thereof.

16. 6-carboxy-2-(2'-ethoxy-5'-ethyl-phenyl)-3,4-dihydro-4-oxo-quinazoline and the pharmaceutically acceptable esters and salts thereof.

17. 6-[2-(N,N-diethylamino)-ethoxy-carbonyl]-2-(2'-ethoxy-3'-methoxy-phenyl)-3,4-dihydro-4-oxo-quinazoline and the pharmaceutically acceptable salts thereof.

18. 6-[2-(N,N-dimethylamino)-ethoxy-carbonyl]-2-(2'-ethoxy-3'-methoxy-phenyl)-3,4-dihydro-4-oxo-quinazoline and the pharmaceutically acceptable salts thereof.

19. 6-[2-(1pyrrolidinyl)-ethoxy-carbonyl]-2-(2'-ethoxy-3'-methoxy-phenyl)-3,4-dihydro-4-oxo-quinazoline and the pharmaceutically acceptable salts thereof.

20. A pharmaceutical composition suitable for the treatment of allergies, comprising a compound of claim 1 and a pharmaceutically acceptable carrier or diluent.

21. A method of treating allergies in a patient in need of such treatment, said method comprising administering to said patient a therapeutically effective amount of a compound of claim 1.

22. A method of claim 21, wherein said compound is administered orally.

* * * * *